United States Patent [19]
Lippitsch et al.

[11] Patent Number: 5,308,581
[45] Date of Patent: May 3, 1994

[54] SUBSTANCE OF AN OPTICAL FLUORESCENCE MEASURING ARRANGEMENT FOR MEASURING THE PH OF A SAMPLE AND OPTICAL SENSOR WITH SUCH AN INDICATOR SUBSTANCE

[75] Inventors: Max Lippitsch; Marco J. Leiner; Hellfried Karpf, all of Graz, Austria

[73] Assignee: AVL Medical Instruments AG, Schaffhausen, Switzerland

[21] Appl. No.: 916,154

[22] PCT Filed: Dec. 12, 1991

[86] PCT No.: PCT/AT91/00128
§ 371 Date: Jul. 31, 1992
§ 102(e) Date: Jul. 31, 1992

[87] PCT Pub. No.: WO92/10739
PCT Pub. Date: Jun. 25, 1992

[30] Foreign Application Priority Data
Dec. 12, 1990 [AT] Austria .................... 2512/90

[51] Int. Cl.⁵ ..................... G02B 6/00; G01N 33/94
[52] U.S. Cl. ..................... 422/82.08; 422/82.06; 422/82.05; 436/169; 359/123
[58] Field of Search ............. 422/82.06, 82.05, 82.08; 436/169, 501; 350/96.29, 96.34

[56] References Cited
U.S. PATENT DOCUMENTS

| | | | |
|---|---|---|---|
| 4,767,718 | 8/1988 | Meyers | 436/501 |
| 4,925,268 | 5/1990 | Iyer et al. | 422/82.06 |
| 5,047,351 | 9/1991 | Makiuchi et al. | 436/169 |

OTHER PUBLICATIONS

Aldrich Catalog; 1988, pp. 33, 34, 60, 147, 152, 174, 416, 552, 977, 1059, 1089, 1304, 1321.
Wolfbeis et al.; "A Study on Fluorescent Indicators . . . "; Fresenius Z Anal. Chem; 314; 1983; 119–124.
Wolfbeis et al.; "Syntheses of Fluorescent Dyes"; Journal of Heterocyclic Chem.; 19; 1982; 841–843.

*Primary Examiner*—Robert J. Warden
*Assistant Examiner*—Ramon Torres
*Attorney, Agent, or Firm*—Watson, Cole, Grindle & Watson

[57] ABSTRACT

An indicator for use in a luminescence-optical configuration for continuous and reversible measurement of the pH of a sample within a relevant measuring range (M), whose luminescence decay time $\tau$ is dependent on the pH of the sample, is characterized by the following properties. The $pK_a$ value of the acidic or basic indicator is in the relevant measuring range when the indicator is in its electronic ground state ($S_0$). The protonation rate $k_p$ of the base, or deprotonation rate $k_{dp}$ of the acid in the excited state ($S_1$, X) of the indicator is lower than the decay rate $k_A$ of the excited state, and the luminescence decay times $\tau_S$ and $\tau_B$ of the acidic forms ($AH^*$, $BH^{+*}$) and the basic forms ($A^{-*}$, $B^*$) of the indicator are different from each other. If the $pK_a\tau$ value of the indicator in its electronically excited state ($S_1$, X) is within the relevant measuring range, the protonation rate $k_p$ of the base, or deprotonation rate $k_{dp}$ of the acid in the excited state ($S_1$, X) of the indicator is higher than the decay rate $k_A$ of the excited state.

20 Claims, 2 Drawing Sheets

SUBSTANCE OF AN OPTICAL FLUORESCENCE MEASURING ARRANGEMENT FOR MEASURING THE PH OF A SAMPLE AND OPTICAL SENSOR WITH SUCH AN INDICATOR SUBSTANCE

BACKGROUND OF THE INVENTION

The invention relates to an indicator for use in a luminescence-optical configuration for continuous and reversible measurement of the pH of a sample within a relevant measuring range, the sample being at least in indirect contact with the indicator provided as an acid or base, and the luminescence decay time $\tau$ of the indicator depending on the pH of the sample, and to a sensor comprising such an indicator.

DESCRIPTION OF THE PRIOR ART

Measuring the pH is an essential task in many fields of science and technology, for instance in chemistry, process engineering, manufacturing or environmental analysis. Optical methods and devices for pH measurement have been proposed frequently. A survey of the latest state of the art is given by LEINER & WOLFBEIS: Fiber Optic pH Sensors, in CRC Book on Fiber Optic Chemical Sensors and Biosensors, O. S. WOLFBEIS (ed.), CRC Press Inc., Boca Raton, Fla. 1991. In particular, two methods have proved useful: pH measurement via the change in absorption, and via the change in luminescence of a suitable indicator. Absorption-optical sensors are simpler in design, but in practice are prone to considerable technical problems (low signal change, high straylight, poor long-term stability, etc.). In luminescence-optical sensors some of these problems are avoided, though their long-term stability often is unsatisfactory, as the concentration of the indicator changes over time due to various influences, thus giving rise to signal changes biasing the measured result.

A method of improving long-term stability of luminescence-optical sensors to a considerable extent, in particular the long-term stability of optical fluorosensors, is characterized by using fluorescence decay time rather than fluorescence intensity for measurement (LIPPITSCH et al., Analytica Chimica Acta 205 (1988), 1-6). As luminescence, or rather, fluorescence decay time is largely independent of indicator concentration, measuring errors due to concentration are eliminated. So far luminescence-optical sensors based on decay time measurement have mainly been developed for measuring physical variables (e.g., temperature) and oxygen concentration. For a long time it has not been possible to produce luminescence-optical pH sensors, as no indicator media were known that would respond to a change in pH by a reversible change in luminescence decay time.

So far only two attempts have been made to develop fluorescence-optical pH sensors based on decay time measurement.

An arrangement is known from AT-PS 393 035, where two substances in close contact with each other are provided in an optical sensor, the first substance being a fluorophore insensitive to the pH value to be determined, and the other one being a chromophore influencing the fluorescence of the fluorophore. The reduction in fluorescence decay time $\tau$ due to the energy transfer between chromophore and fluorophore is employed for quantitative determination of the pH value. The extent of energy transfer is determined by the overlap of the fluorescence spectrum of the fluorophore (donor) and the absorption spectrum of the pH indicator (acceptor) and their distance in space, and is thus dependent on the spatial distribution and the concentration of the two substances. In this way the major advantage of decay time sensors, i.e. their independence of indicator concentration, is lost.

The second attempt at developing a decay time sensor for pH measurement is described in "New luminescent metal complex for pH transduction in optical fiber sensing", by M. C. MORENO-BONDI et al., SPIE 1368, 1990, 157-164. In this device an indicator material is used, for instance, a ruthenium complex, whose fluorescence is dynamically quenched by acids, which will result in a change in fluorescence decay time. The degree of quenching, however, is determined by the type and concentration of the buffer, as well as by the chemical composition of the quenching acid, and only indirectly by the pH value. For this reason use of the device as a pH sensor is of limited value only.

| LIST OF ABBREVIATIONS | |
|---|---|
| * | electronically excited state |
| [ ] | concentration |
| AH | acid |
| A$^-$ | conjugate base |
| H$^+$ | proton |
| pH = $-\log$(H$^+$) | pH value |
| B | base |
| BH$^+$ | conjugate base |
| Ka | acid constant (dissociation equilibrium constant of an acid) |
| pKa = $-\log$(Ka) | pK value of an acid or conjugate acid |
| kR | radiation decay rate |
| kc | radiationless deexcitation rate (S$_1$ — S$_0$ internal conversion or S$_1$ — T$_1$ intersystem crossing) |
| kA | decay rate of the excited state (luminescence decay rate) kA = kR + kc |
| $\tau$ | lifetime of the excited state (luminescence decay time) $\tau$ = 1/kA |
| ks 1x | radiationless conversion rate from the electronically excited state S$_1$ to an electronically excited state X |
| kp | protonation rate |
| kd p | deprotonation rate |

In the following the BRONSTED-LOWRY definition of acids and bases is used:

| reaction | acid constant |
|---|---|
| Acids | |
| AH <=> A$^-$ + H$^+$ | $K_a = \dfrac{[A^-][H^+]}{[AH]}$ |
| Bases | |
| BH$^+$ <=> B + H$^+$ | $K_a = \dfrac{[B][H^+]}{[BH^+]}$ |

SUMMARY OF THE INVENTION

It is an object of the invention to avoid the disadvantages of known decay time sensors for pH measurement and to propose indicator materials permitting direct determination of the pH value.

In the invention this object is achieved by providing that (1) the pK$_a$ value of the indicator in its electronic ground state (S$_0$) be in the relevant measuring range, and that the protonation rate k$_p$ of the base or deprotonation rate $k_{dp}$ of the acid in the excited state ($S_1$, X) of the indicator be lower than the decay rate $k_A$ of the excited state, and, further, that the luminescence decay times $\tau_S$ and $\tau_B$ of the acidic forms (AH*, BH+*) and basic forms (A−*, B*) of the indicator differ from each other, or that (2) the $pK_a^*$ value of the indicator in its electronically excited state ($S_1$, X) be in the relevant measuring range, and that the protonation rate $k_p$ of the base or deprotonation rate $k_{dp}$ of the acid in the excited state ($S_1$, X) of the indicator be higher than the decay rate $k_A$ of the excited state, and, further, that the luminescence decay times $\tau_S$ and $\tau_B$ of the acidic forms (AH*, BH+*) and basic forms (S−*, B*) of the indicator differ from each other. In both fundamental instances the measured luminescence decay time $\tau$ is a function of the luminescence decay times $\tau_B$ and $\tau_S$, their weighting depending on the pH prevailing in the sample.

Figure 1:
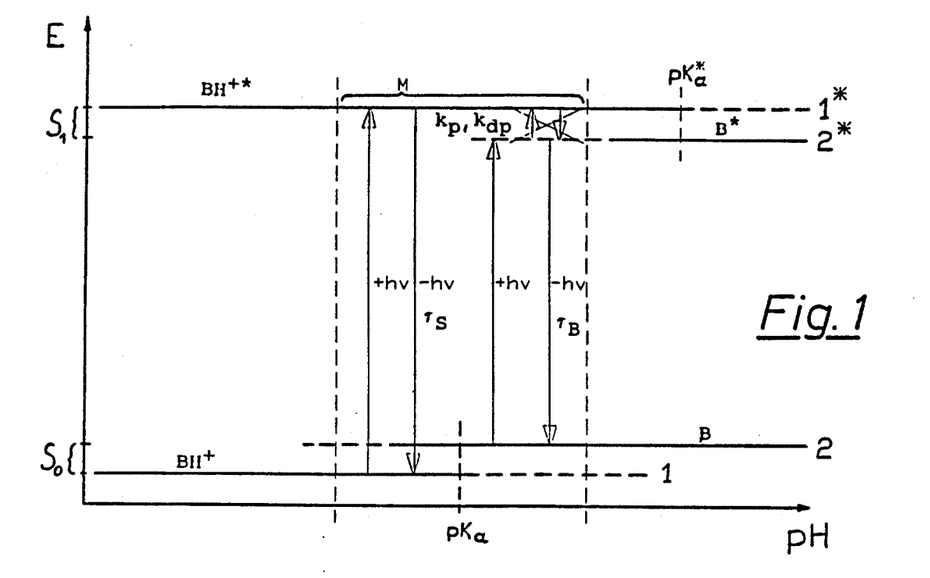
FIGS. 1 and 2 are diagrams in which the pH value is plotted along the x-axis, and the energy level E along the y-axis, in arbitrary units.
Figure 2:
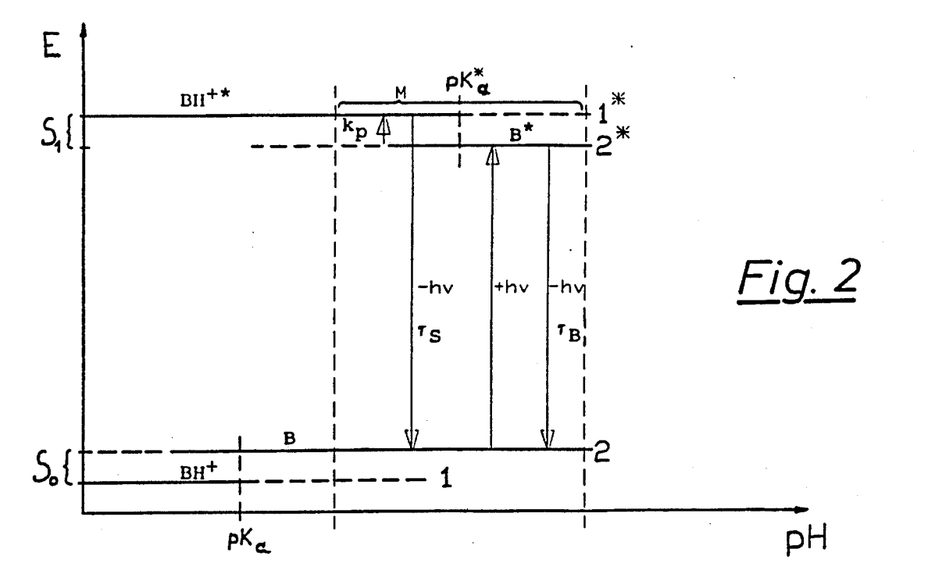
Figure 3:
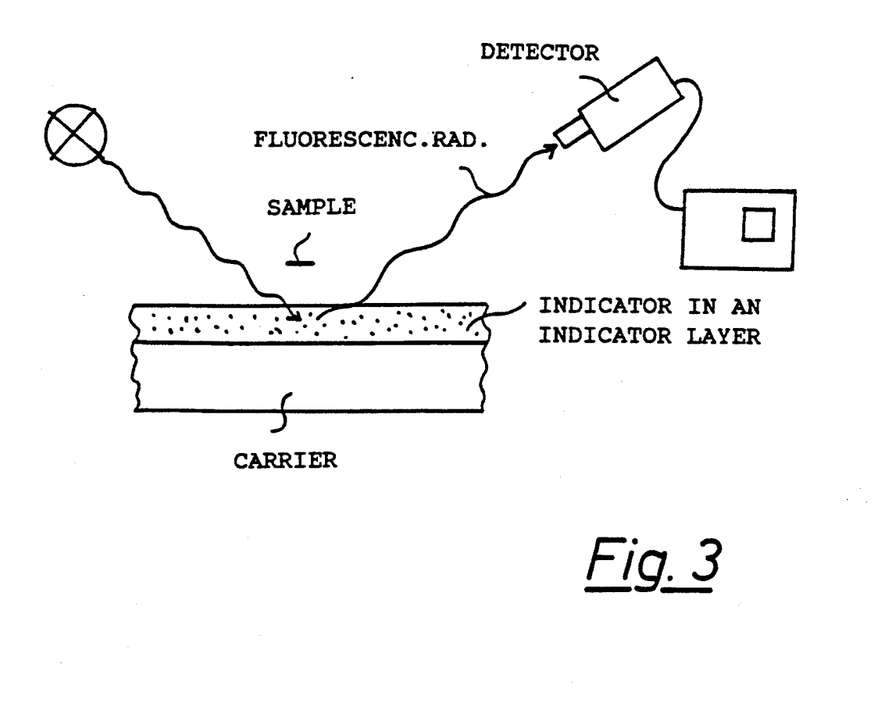
FIG. 3 is a schematic representation of a sensor according to the invention.

The essential properties of the indicator materials described by the invention are presented in the diagrams of FIGS. 1 and 2.

Individual groups of indicator materials may be differentiated by the manner in which the different luminescence decay times $\tau_B$ and $\tau_S$ arise.

For a first group the invention proposes that at least two excited states ($S_1$, X) of the neutral form of the indicator (base B* or acid AH*) should be in reverse order relative to each other as compared to the corresponding excited states of the ionic form of the indicator (conjugate acid BH+* or conjugate base A−*), and that the radiationless conversion rate between the two or more excited states of the neutral form should exceed the decay rate $k^A$ of the excited states of the neutral form.

For a second group the invention proposes that the radiation decay rates $k^R$ of the excited neutral form of the indicator (base B* or acid AH*) and the excited ionic form of the indicator (conjugate acid BH+*) or conjugate base A−*) differ from each other.

Finally, a third group of indicator materials is characterized by the radiationless deexcitation rate $k_C$ of the excited neutral form of the indicator (base B* or acid AH*) being different from that of the excited ionic form of the indicator (conjugate acid BH+* or conjugate base A−*).

According to the invention a luminescence-optical sensor for continuous and reversible measurement of the pH of a sample is provided with an indicator of one of the above three groups.

The following pages contain a list of the criteria or characteristics for selection of pH-sensitive indicators whose luminescence decay time $\tau$ is directly and reversibly dependent on the pH of a sample.

1. Indicator protonation or dissociation in the ground state

The $pK_a$ value of the electronically non-excited acid (AH or BH+) is in the relevant measuring range.

1.1 Indicator bases (B)

The deprotonation rate $k_{dp(BH+^* \rightarrow B^* + H+)}$ of the electrically excited conjugate acid (BH*) is lower than its luminescence decay rate $K_{A(BH+^* \rightarrow BH+ + h\nu)}$.

The luminescence decay rate $k_{A(B^* \rightarrow B + h\nu)}$ of the electronically excited base (B*) is high compared to its protonation rate $k_{p(B^* + H+ \rightarrow BH+^*)}$.

1.1.a

At least two states (e.g., $\pi-\pi^*$ and $n-\pi^*$) of the electronically excited base (B*) have reverse energetic positions relative to each other, as compared to the corresponding states of the electronically excited conjugate acid (BH+*). The radiationless conversion rate $k_{S1X(S1(BH+^*) \rightarrow X(BH+^*))}$ is higher than the luminescence decay rate $k_A$ of the excited state $S_1$ (BH+*), which will give different luminescence decay times ($\tau$) of the excited states (BH+* and B*).

1.1.b

The luminescence decay rate $k_{A(B^* \rightarrow B+h\nu)}$ of the electronically excited base (B*) and the luminescence decay rate $k_{A(BH+^* \rightarrow BH+ + h\nu)}$ of the electronically excited conjugate acid (BH+*) differ from each other (for example, due to different transition probabilities and similarly high quantum yield of the two forms), which will give different luminescence decay times ($\tau$) of the excited states (BH+* and B*).

1.1.c

The radiationless deexcitation rate $k_{C(B^* \rightarrow B)}$ of the excited base (B*) differs from the radiationless deexcitation rate $k_{C(BH+^* \rightarrow BH+)}$ of the excited conjugate acid (BH+*), which will give different luminescence decay times ($\tau$) of the excited states (BH+* and B*).

1.2 Indicator acids (AH)

The protonation rate $Kp_{(A^{-*} + H+ - AH^*)}$ of the conjugate base (A−*) in the electronically excited state is lower than its luminescence decay rate $k_{A(A-^* \rightarrow A- + h\nu)}$.

The luminescence decay rate $k_{A(AH^* \rightarrow AH + h\nu)}$ of the electronically excited acid (AH*) is high compared to its deprotonation rate $k_{dp(AH^* \rightarrow A-^* + H+)}$.

1.2.a

At least two states (e.g., $\pi-\pi^*$ and $n-\pi^*$) of the electronically excited acid (AH*) have reverse energetic positions relative to each other, as compared to the corresponding states of the electronically excited conjugate base (A−*). The radiationless conversion rate $k_{S1X(S1(AH^*) \rightarrow X(AH^*))}$ is higher than the luminescence decay rate $k_A$ of the excited state $S_1$ (AH*), which will give different luminescence decay times ($\tau$) of the excited states (AH* and A−*).

1.2.b

The luminescence decay rate $k_{A(AH^* \rightarrow AH + h\nu)}$ of the electronically excited acid (AH*) and the luminescence decay rate $k_{A(A-^* \rightarrow A- + h\nu)}$ of the electronically excited conjugate base (A−*) differ from each other (for example, due to different transition probabilities and similarly high quantum yield of the two forms), which will give different luminescence decay times ($\tau$) of the excited states (AH* and A−*).

1.2.c

The radiationless deexcitation rate $k_{C(AH^* \rightarrow AH)}$ of the excited acid (AH*) differs from the radiationless deexcitation rate $k_{C(A-^* \rightarrow A-)}$ of the excited conjugate base (A−*), which will give different luminescence decay times ($\tau$) of the excited states (AH* and A−*).

2. Indicator protonation or dissociation in the excited state

The $pK_a^*$ value of the electronically excited acid (AH* or BH+*) is in the relevant measuring range.

2.1 Indicator bases

The $pK_a$ value of the conjugate acid (BH+) in its electronic ground state is smaller than the lower limit of the relevant measuring range.

The luminescence decay rate $k_{A(B^* \rightarrow B + h\nu)}$ of the electronically excited base (B*) is lower than its protonation rate $k_{p(B^* + H^+ \rightarrow BH^{+*})}$, which will lead to a protonation in the electronically excited state.

2.1.a

At least two states (e.g., $\pi-\pi^*$ and $n-\pi^*$) of the electronically excited conjugate acid (BH+*) have reverse energetic positions relative to each other, as compared to the corresponding states of the electronically excited base (B*). The radiationless conversion rate $k_{S1X(S1(BH^{+*}) \rightarrow X(BH^{+*}))}$ is higher than the luminescence decay rate $k_A$ of the excited state $S_1$ (BH+*), which will result in different luminescence decay times ($\tau$) of the excited states (BH+* and B*).

2.1.b

The luminescence decay rate $k_{A(B^* \rightarrow B + h\nu)}$ of the electronically excited base (B*) and the luminescence decay rate $k_{A(BH^{+*} \rightarrow BH^+ + h\nu)}$ of the electronically excited conjugate acid (BH+*) differ from each other (for example, due to different transition probabilities and similarly high quantum yield of the two forms), which will result in different luminescence decay times ($\tau$) of the excited states (BH+* and B*).

2.1.c

The radiationless deexcitation rate $k_{C(B^* \rightarrow B)}$ of the excited base (B*) differs from the radiationless deexcitation rate $k_{C(BH^{+*} \rightarrow BH^+)}$ of the excited conjugate acid (BH+*), which will result in different luminescence decay times ($\tau$) of the excited states (BH+* and B*).

2.2 Indicator acids

The $pK_a$ value of the acid (AH) in its electronic ground state is higher than the upper limit of the relevant measuring range.

The luminescence decay rate $k_{A(AH^* \rightarrow AH + h\nu)}$ of the electronically excited acid (AH*) is lower than its deprotonation rate $k_{dp(AH^* \rightarrow A^{-*} + H^+)}$, which will lead to a deprotonation in the electronically excited state.

2.2.a

At least two states (e.g., $\pi-\pi^*$ and $n-\pi^*$) of the electronically excited acid (AH*) have reverse energetic positions relative to each other, as compared to the corresponding states of the electronically excited conjugate base (A−*). The radiationless conversion rate $k_{S1X(S1(AH^*) \rightarrow X(AH^*))}$ is higher than the luminescence decay rate $k_A$ of the excited state $S_1$(AH*), which will result in different luminescence decay times ($\tau$) of the excited states (AH* and A−*).

2.2.b

The luminescence decay rate $k_{A(AH^* \rightarrow AH + h\nu)}$ of the electronically excited acid (AH*) and the luminescence decay rate $k_{A(A^{-*} \rightarrow A^- + h\nu)}$ of the electronically excited conjugate base (A−*) differ from each other (for example, due to different transition probabilities and similarly high quantum yield of the two forms), which will result in different luminescence decay times ($\tau$) of the excited states (AH* and A−*).

2.2.c

The radiationless deexcitation rate $k_{C(AH^* \rightarrow AH)}$ of the excited acid (AH*) differs from the radiationless deexcitation rate $k_{C(A^{-*} \rightarrow A^-)}$ of the excited conjugate base (A−*), which will result in different luminescence decay times ($\tau$) of the excited states (AH* and A−*).

Suitable substances meeting the criteria listed under items 1 and 2 are found among indicator bases containing aliphatic or aromatic amino groups (—NH$_2$, —NRH, —NR$_2$), or heterocyclic nitrogen compounds (=N—), for example. With decreasing pH values of the solution the above materials are capable of binding protons to the free electron pair of the nitrogen atom.

Other suitable substances are found among indicator acids containing phenolic hydroxyl groups (—OH), or carboxylic acid groups (—COOH), for example. With increasing pH values of the solution these materials will liberate protons.

Any other acid/base-indicators meeting the above criteria are less simple to define. The pH-dependent change in spectral properties takes place via a molecular transformation. This transformation may occur via several intermediates.

Further suitable indicators are coumarins, fluoresceins, naphthyl and pyrene derivatives, for instance, which have previously been discussed in the literature on fluorescence intensity measurement.

Possible substituents for influencing the pK value of the indicator would be —CH$_3$, —CF$_3$, cyano, carboxy, carboxyamido, phenyl, and higher halides.

As chromophoric molecular moieties of the indicators homo- or heterocyclic (mono- or polycyclic) aromatic hydrocarbons may be used.

In an embodiment of the invention referring to item 1, the indicator is immobilized on a solid substrate, for example, and is brought into contact with the sample. Fluorescence is excited with a short-time light source (e.g., a coaxial flashlamp, a pulsed laser, a pulsed light-emitting diode), either (if the absorption spectra of neutral form and ionic form do not overlap) over such a broad band of the spectrum that the excitation spectrum will cover the absorption of the indicator in both the ionic and the neutral form, or (if there is an overlap of the absorption spectra of the two forms) over a narrow band of the spectrum lying within the wavelength range of the overlap region. After separation of the exciting light by means of a cut-off filter, fluorescence is detected over a broad band of the spectrum (for instance, by means of a photomultiplier or a pin photodiode) and decay time is measured electronically. As dissociation takes place in the ground state, both the absorption spectrum and the fluorescence spectrum are modified, which will have no negative effect on the measurement, however, due to the broad-band character of excitation and detection, or rather, due to the choice of the excitation wavelength in the overlap region of the absorption spectra and the broad detection band. Via a stored calibrating function the recorded decay times may be converted into pH values by a computer.

Practical examples of suitable indicators of the invention, including an explanation of their action, will be given below.

EXAMPLE 1.1.B

Indicator Base Acridine

| | |
|---|---|
| excitation/emission maximum conjugate acidic form | 356/475 nm |
| excitation/emission maximum basic form | 356/430 nm |
| measuring range | pH 4.0–7.0 |
| $pK_a$ acidic form (BH+) in ground state | 5.45 |
| $pK_a*$ acidic form (BH+*) in excited state | 10.7 |
| luminescence decay times excited states | |
| $\tau_{(BH+*)} =$ | 33 ns |
| $\tau_{(B*)} =$ | 14 ns |

EXAMPLE 1.2.A

Indicator Acid Salicylaldehyde

| | |
|---|---|
| excitation/emission maximum acidic form | 327/525 nm |
| excitation/emission maximum conjugate basic form | 380/400 nm |
| measuring range | pH 7–10 |
| $pK_a$ acidic form (AH) in ground state | 8.5 approx |
| $pK_a*$ acidic form (AH*) in excited state | 2 approx |
| luminescence decay times excited states | |
| $\tau_{(AH*)} =$ | <<1 ns |
| $\tau_{(A-*)} =$ | 3 ns appr |

In the measuring range (pH 4–7) both forms (BH+ and B) are present. The $pK_a*$ value in the excited state exceeds the $pK_a$ value in the ground state by 5.25 units. For this reason no deprotonation of the conjugate acid (BH+*) takes place in the excited state. The luminescence decay rate $k_A$ of the electronically excited base (B*) is higher than its protonation rate $k_p$. The luminescence decay rate $k_A$ of the electronically excited base (B*) and that of the electronically excited conjugate acid (BH+*) differ from each other, yielding different luminescence decay times of the excited states ($\tau_{(BH+*)} = 33$ ns, $\tau_{(B*)} = 14$ ns).

In the measuring range (pH 7–10) both forms (AH and A−) are present. The $pK_a*$ value in the excited state is lower than the $pK_a$ value in the ground state by approx. 6.5 units. For this reason no protonation of the conjugate base (A−*) takes place in the excited state. The luminescence decay rate $k_A$ of the electronically excited acid (AH*) is higher than its deprotonation rate $k_{dp}$. Two states ($\pi - \pi*$ and $n - \pi*$) of the electronically excited acid (AH*) have reverse energetic positions relative to each other, as compared to the corresponding states of the electronically excited conjugate base (A−*). The radiationless conversion rate $k_{S1X(S1(AH^*) \to X(AH^*))}$ is higher than the luminescence decay rate $k_A$ of the excited state $S_1(AH^*)$, which will result in different luminescence decay times ($\tau$) of the excited states ($\tau_{(AH^*)} < 1$ ns, $\tau_{(A^{-*})} = 3$ ns approx.)

EXAMPLE 1.2.c

Indicator acid 3-indolylacetic acid

| | |
|---|---|
| excitation/emission maximum acidic form | 278/340 nm |
| excitation/emission maximum conjugate basic form | 285/340 nm |
| measuring range | pH 2–4 |
| $pK_a$ acidic form (AH) in ground state | 3 approx |
| $pK_a^*$ acidic form (AH*) in excited state | 2 approx |
| luminescence decay times excited states | |
| $\tau_{(AH^*)} =$ | 2.5 ns |
| $\tau_{(A^{-*})} =$ | 9.0 ns |

In the measuring range (pH 2–4) both forms (AH and $A^-$) are present. The pKa* value in the excited state is lower than the pKa value in the ground state by approx. 2 units. For this reason no protonation of the conjugate base ($A^{-*}$) takes place in the excited state. The luminescence decay rate $k_A$ of the electronically excited acid (AH*) is higher than its deprotonation rate $k_{dp}$. The radiationless deexcitation rate $k_C$ of the electronically excited acid (AH*) differs from the radiationless deexcitation rate $k_c$ of the electronically excited conjugate base ($A^{-*}$), which will give different luminescence decay times of the excited states $\tau_{(AH^*)} = 2.5$ ns, $\tau_{(A^{-*})} = 9.0$ ns).

Other examples of indicators whose luminescence decay time is influenced by acid-base reactions in the electronic ground state, include

| | |
|---|---|
| re 1.1.b | 9-aminoacridine |
| re 1.2.a | 1-hydroxyacetyl-naphthalene |
| | dihydroxyanthraquinone |
| | 4-hydroxybenzonitrile |
| | 9-chloro-10-diethylaminomethylanthrazene |
| re 1.2.b | benzothiazole derivatives |
| | benzooxazole derivatives |
| | benzimidazole derivatives |
| | azaindole |
| | methyl salicylate |
| | harman |
| | norharman |
| | salicylamide |
| re 1.2.c | biliverdin derivatives |
| | porphyrin derivatives |

In an embodiment of the invention referring to item 2, a suitable indicator is immobilized on a solid substrate, and is dipped into the sample. Excitation takes place monochromatically with the use of a short-time light source (e.g., a coaxial flashlamp) and a color filter tuned to the absorption wavelength of the indicator (e.g., an interference filter). After separation of the exciting light by means of a cut-off filter, emission is detected over a broad band of the spectrum (for instance, by means of a photomultiplier or a pin photodiode). The pH value again is determined from the measured decay time via a stored calibrating function.

Practical examples of suitable indicators of the invention, including an explanation of their action, will be given below.

EXAMPLE 2.1.b

Indicator base 9(10H)-acridone

| | |
|---|---|
| excitation/emission maximum conjugate acidic form | 399/456 nm |
| excitation/emission maximum basic form | 383/440 nm |
| measuring range | pH 0.5–2.5 |
| $pK_a$ acidic form (BH+) in ground state | 0.02 |
| $pK_a^*$ acidic form (BH+*) in excited state | 1.7 |
| luminescence decay times excited states | |
| $\tau_{(BH+^*)} =$ | 15 ns |
| $\tau_{(B^*)} =$ | 26 ns |

-continued

In the measuring range (pH 0.5-2.5) the basic form (B) is predominating. The pKa* value in the excited state exceeds the pKa value in the ground state by 1.7 units. For this reason it is mainly the basic form (B) that is excited in the relevant measuring range. The luminescence decay rate $k_A$ of the electronically excited base (B*) is lower than its protonation rate $k_p$, so that a protonation of the base (B*) takes place in the electronically excited state. The luminescence decay rate $k_A$ of the electronically excited base (B*) and that of the electronically excited conjugate acid (BH+*) differ from each other, yielding different luminescence decay times of the excited states ($\tau_{(BH+*)}=15$ ns, $\tau_{(B*)}=26$ ns).

EXAMPLE 2.2.b

Indicator acid 2-naphthol

| | |
|---|---|
| excitation/emission maximum acidic form | 328/356 nm |
| excitation/emission maximum conjugate basic form | 348/410 nm |
| measuring range | pH 1.2–4.3 |
| pK$_a$ acidic form (AH) in ground state | 9.8 approx |
| pK$_a$* acidic form (AH*) in excited state | 2.8 approx |
| luminescence decay times excited states | |
| $\tau_{(AH*)} =$ | 9.0 ns |
| $\tau_{(A-*)} =$ | 4.8 ns |

In the measuring range (pH 1.2–4.3) only the acidic form (AH) is present. The pKa* value in the excited state is smaller than the pKa value in the ground state by 7 units. For this reason only the acidic form (AH) is excited in the relevant measuring range. The luminescence decay rate $k_A$ of the electronically excited acid (AH*) is lower than its deprotonation rate $k_{dp}$, so that a deprotonation takes place in the electronically excited state. The luminescence decay rate $k_A$ of the electronically excited acid (AH*) and that of the electronically excited conjugate base (A−*)) differ from each other, yielding different luminescence decay times of the excited states ($\tau_{(AH*)}=9.0$ ns, $\tau_{(A-*)}=4.8$ ns).

Other examples of indicators whose luminescence decay time is influenced by acid-base reactions in the electronically excited state, are

| | |
|---|---|
| re 2.1.a | quinidine |
| | quinine |
| re 2.1.b | 6-methoxyquinoline |
| re 2.2.b | 1-hydroxypyrene |
| | 1-hydroxypyrene-3,6,8-trisulphonic acid |
| | 5-aminoindazole |

DESCRIPTION OF THE DRAWINGS

The invention will be further described with reference to the accompanying drawings, in which.

In FIG. 1 protonation or dissociation of the indicator takes place in the ground state $S_0$. The pK$_a$ value is in the relevant measuring range M. The ground states of the conjugate acid BH+ and the base B of the indicator have the reference numbers 1 and 2; for the excited state $S_1$ the respective reference numbers are 1* and 2*. In the example of an indicator base shown here, the pK$_a$* value is above the measuring range on the pH scale. In the instance of an indicator acid, however, the pK$_a$* value is below the measuring range M.

In FIG. 2 protonation $k_p$ of the indicator base B* takes place in the excited state $S_1$. The pK$_a$* value is in the relevant measuring range M. The pK$_a$ value in the ground state is below the relevant measuring range M.

In both FIGS. 1 and 2 decay times $\tau_B$ and $\tau_S$ are different from each other. In both fundamental instances the measured luminescence decay time $\tau$ is a function of the luminescence decay times $\tau_B$ and $\tau_S$, their weighting depending on the pH prevailing in the sample.

We claim:

1. A luminescence-optical indicating substance for continuous and reversible measurement of the pH value of a sample within a measuring range M of interest, said sample being at least in indirect contact with said indicating substance provided as a base $B^*$, having a luminescence decay time $\tau$ depending on the pH value of said sample, comprising
   a) a $pK_a$ value, in an electric ground state as $S_0$, which lies in said measuring range M of interest;
   b) a protonation rate $k_p$ of said base $B^*$ and a deprotonation rate $k_{dp}$ of conjugate acid $BH^{+*}$ in an excited state $S_1$ lower than a decay rate $k_A$ of said excited state; and
   c) luminescence decay times $\tau_S$ and $\tau_B$ of said conjugate acid $BH^{+*}$ and said base $B^*$ which differ from each other.

2. An indicating substance according to claim 1, wherein at least two of said excited states of said indicator base $B^*$ are in reverse order relative to each other as compared to corresponding excited states of said conjugate acid $BH^{+*}$, and wherein a radiationless conversion rate between said at least two excited states of said indicator base $B^*$ exceeds said decay rate $k_A$ of said excited states of said indicator base $B^*$.

3. An indicating substance according to claim 1, wherein radiation decay rates $k_R$ of said excited indicator base $B^*$ and of said excited conjugate acid $BH^{+*}$ differ from each other.

4. An indicating substance according to claim 1, wherein a radiationless deexcitation rate $k_C$ of said excited indicator base $B^*$ is different from that of said excited conjugate acid $BH^{+*}$.

5. A luminescence-optical sensor for continuous and reversible measurement of the pH value of a sample using a chemically or physically immobilized indicator according to claim 1.

6. A luminescence-optical indicating substance for continuous and reversible measurement of the pH value of a sample within a measuring range M of interest, said sample being at least in indirect contact with said indicating substance provided as an acid $AH^*$, having a luminescence decay time $\tau$ depending on the pH value of said sample, comprising
   a) a $pK_a$ value, in an electronic ground state as $S_0$, which lies in said measuring range M of interest;
   b) a deprotonation rate $k_{dp}$ of said acid $AH^*$ and a protonation rate $k_p$ of conjugate base $A^{-*}$ in an excited state $S_1$ lower than a decay rate of $k_A$ of said excited state; and
   c) luminescence decay times $\tau_S$ and $\tau_B$ of said acid $AH^*$ and said conjugate base $A^{-*}$ which differ from each other.

7. An indicating substance according to claim 6, wherein at least two of said excited states of said indicator acid $AH^*$ are in reverse order relative to each other as compared to corresponding excited states of said conjugate base $A^{-*}$, and wherein a radiationless conversion rate between said at least two excited states of said indicator acid $AH^*$ exceeds said decay rate $k_A$ of said excited states of said indicator acid $AH^*$.

8. An indicating substance according to claim 6, wherein radiation decay rates $k_R$ of said excited indicator acid $AH^*$ and of said excited conjugate base $A^{-*}$ differ from each other.

9. An indicating substance according to claim 6, wherein radiationless deexcitation rate $k_c$ of said excited indicator acid $AH^*$ is different from that of said excited conjugate base $A^{-*}$.

10. A luminescence-optical sensor for continuous and reversible measurement of the pH value of a sample using a chemically or physically immobolized indicator according to claim 6.

11. A luminescence-optical indicating substance for continuous and reversible measurement of the pH value of a sample within a measuring range M of interest, said sample being at least in indirect contact with said indicating substance provided as a base $B^*$, having a luminescence decay time $\tau$ depending on the pH value of said sample, comprising
    a) a $pK_a^*$ value, in an electronic ground state as $S_1$, which lies in said measuring range M of interest;
    b) a protonation rate $k_p$ of said base $B^*$ in said excited state $S_1$ higher than a decay rate $k_A$ of said excited state; and
    c) luminescence decay times $\tau_S$ and $\tau_B$ of conjugate acid $BH^{+*}$ and said base $B^*$ which differ from each other.

12. An indicating substance according to claim 11, wherein at least two of said excited states of said indicator base $B^*$ are in reverse order relative to each other as compared to corresponding excited states of said conjugate acid $BH^{+*}$, and wherein a radiationless conversion rate between said at least two excited states of said indicator base $B^*$ exceeds said decay rate $k_A$ of said excited states of said indicator base $B^*$.

13. An indicating substance according to claim 11, wherein radiation decay rates $k_R$ of said excited indicator base $B^*$ and of said excited conjugate acid $BH^{+*}$ differ from each other.

14. An indicating substance according to claim 11, wherein a radiationless deexcitation rate $k_C$ of said excited indicator base $B^*$ is different from that of said excited conjugate acid $BH^{+*}$.

15. A luminescence-optical sensor for continuous and reversible measurement of the pH value of a sample using a chemically or physically immobilized indicator according to claim 11.

16. A luminescence-optical indicating substance for continuous and reversible measurement of the pH value of a sample within a measuring range M of interest, said sample being at least in indirect contact with said indicating substance provided as an acid $AH^*$, having a luminescence decay time $\tau$ depending on the pH value of said sample, comprising
    a) a $pK_a^*$ value, in which an electronic ground state as $S_1$, which lies in said measuring range M of interest;
    b) a deprotonation rate $k_{dp}$ of said acid $AH^*$ in said excited state $S_1$ higher than a decay rate $k_A$ of said excited state; and
    c) luminescence decay times $\tau_S$ and $\tau_B$ of said acid $AH^*$ and conjugate base $A^{-*}$ which differ from each other.

17. An indicating substance according to claim 16, wherein at least two of said excited states of said indicator acid $AH^*$ are in reverse order relative to each other as compared to corresponding excited states of said conjugate base $A^{-*}$, and wherein a radiationless conversion rate between said at least two excited states of said indicator acid $AH^*$ exceeds said decay rate $k_A$ of said excited states of said indicator acid $AH^*$.

18. An indicating substance according to claim 16, wherein radiation decay rates $k_R$ of said excited indicator acid $AH^*$ and of said excited conjugate base $A^{-*}$ differ from each other.

19. An indicating substance according to claim 16, wherein a radiationless deexcitation rate $k_C$ of said excited indicator acid AH* is different from that of said excited conjugate base A$^{-*}$.

20. A luminescence-optical sensor for continuous and reversible measurement of the pH value of a sample using a chemically or physically immobilized indicator according to claim 16.

* * * * *